US009011427B2

(12) United States Patent
Price et al.

(10) Patent No.: US 9,011,427 B2
(45) Date of Patent: Apr. 21, 2015

(54) SURGICAL INSTRUMENT SAFETY GLASSES (75) Inventors: Daniel W. Price, Loveland, OH (US);
Cory G. Kimball, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 44 days.

(21) Appl. No.: 13/276,687

(22) Filed: Oct. 19, 2011

(65) Prior Publication Data

US 2012/0116365 A1 May 10, 2012

Related U.S. Application Data (60) Provisional application No. 61/410,603, filed on Nov. 5, 2010, provisional application No. 61/487,846, filed on May 19, 2011.

(51) Int. Cl.
*A61B 18/12* (2006.01)
*A61B 18/14* (2006.01)
(Continued)

(52) U.S. Cl.
CPC .............. *A61B 18/1442* (2013.01); *H01M 2/26* (2013.01); *H01M 2/10* (2013.01); *A61B 18/1206* (2013.01); *A61B 19/56* (2013.01); *A61B 17/00234* (2013.01); *A61B 17/064* (2013.01); *A61B 17/285* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/1233* (2013.01); *A61B 18/14* (2013.01); *A61B 18/1445* (2013.01); *A61B 19/38* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/2929* (2013.01); *A61B 2017/293* (2013.01); *A61B 2017/2931* (2013.01);
(Continued)

(58) Field of Classification Search
USPC ........................................................ 606/1–52
See application file for complete search history.

(56) References Cited

U.S. PATENT DOCUMENTS 1,754,806 A 4/1930 Stevenson
3,297,192 A 1/1967 Swett
(Continued)

FOREIGN PATENT DOCUMENTS

DE 102008051866 10/2010
DE 102009013034 10/2010
(Continued)

OTHER PUBLICATIONS

International Search Report and Written Opinion dated Jan. 26, 2012 for Application No. PCT/US2011/059212.
(Continued)

*Primary Examiner* — Aaron Roane (57) ABSTRACT

A surgical instrument includes a handle assembly housing a wireless circuit board. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon.

14 Claims, 6 Drawing Sheets

(51) Int. Cl.
*A61B 17/00* (2006.01)
*A61B 17/32* (2006.01)
*A61B 18/00* (2006.01)
*A61B 18/04* (2006.01)
*H02J 7/00* (2006.01)
H01M 2/26 (2006.01)
H01M 2/10 (2006.01)
A61B 19/00 (2006.01)
A61B 17/064 (2006.01)
A61B 17/285 (2006.01)
A61B 17/29 (2006.01)

(52) U.S. Cl.
CPC ... *A61B 2017/2933* (2013.01); *A61B 2017/294* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H02J 7/0045* (2013.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |

(56) References Cited

U.S. PATENT DOCUMENTS

| | | | |
|---|---|---|---|
| 7,364,061 B2 | 4/2008 | Swayze et al. | |
| 7,364,554 B2 | 4/2008 | Bolze et al. | |
| 7,381,209 B2 | 6/2008 | Truckai et al. | |
| 7,416,101 B2 | 8/2008 | Shelton, IV et al. | |
| 7,422,139 B2 | 9/2008 | Shelton, IV et al. | |
| 7,464,846 B2 | 12/2008 | Shelton, IV et al. | |
| 7,473,145 B2 | 1/2009 | Ehr et al. | |
| 7,479,152 B2 | 1/2009 | Fulton, III et al. | |
| 7,494,492 B2 | 2/2009 | Da Silva et al. | |
| D594,983 S | 6/2009 | Price et al. | |
| 7,563,142 B1 | 7/2009 | Wenger et al. | |
| 7,583,564 B2 | 9/2009 | Ketahara et al. | |
| 7,638,958 B2 | 12/2009 | Philipp et al. | |
| 7,643,378 B2 | 1/2010 | Genosar | |
| 7,717,312 B2 | 5/2010 | Beetel | |
| 7,721,936 B2 | 5/2010 | Shelton, IV et al. | |
| 7,738,971 B2 | 6/2010 | Swayze et al. | |
| 7,766,910 B2 | 8/2010 | Hixson et al. | |
| 7,766,929 B2 | 8/2010 | Masuda | |
| 7,770,722 B2 | 8/2010 | Donahoe et al. | |
| 7,770,775 B2 | 8/2010 | Shelton et al. | |
| 7,776,037 B2 | 8/2010 | Odom | |
| 7,780,660 B2 | 8/2010 | Bourne et al. | |
| 7,815,658 B2 | 10/2010 | Murakami | |
| 7,845,537 B2 | 12/2010 | Shelton, IV et al. | |
| 7,846,155 B2 | 12/2010 | Houser et al. | |
| 7,846,159 B2 | 12/2010 | Morrison et al. | |
| 7,889,489 B2 | 2/2011 | Richardson et al. | |
| 7,922,063 B2 | 4/2011 | Zemlok et al. | |
| 7,948,208 B2 | 5/2011 | Partovi et al. | |
| 7,952,322 B2 | 5/2011 | Partovi et al. | |
| 7,952,873 B2 | 5/2011 | Glahn et al. | |
| 7,959,050 B2 | 6/2011 | Smith et al. | |
| 8,038,025 B2 | 10/2011 | Stark et al. | |
| 8,040,107 B2 | 10/2011 | Ishii | |
| 8,052,605 B2 | 11/2011 | Muller et al. | |
| 8,058,771 B2 | 11/2011 | Giordano et al. | |
| 8,075,530 B2 | 12/2011 | Taylor et al. | |
| 8,097,011 B2 | 1/2012 | Sanai et al. | |
| 8,142,461 B2 | 3/2012 | Houser et al. | |
| 8,147,488 B2 | 4/2012 | Masuda | |
| 8,177,776 B2 | 5/2012 | Humayun et al. | |
| 8,195,271 B2 | 6/2012 | Rahn | |
| 8,210,411 B2 | 7/2012 | Yates et al. | |
| 8,216,212 B2 | 7/2012 | Grant et al. | |
| 8,221,418 B2 | 7/2012 | Prakash et al. | |
| 8,240,498 B2 | 8/2012 | Ramsey et al. | |
| 8,246,642 B2 | 8/2012 | Houser et al. | |
| 8,251,994 B2 | 8/2012 | Mckenna et al. | |
| 8,267,094 B2 | 9/2012 | Danek et al. | |
| 8,277,446 B2 | 10/2012 | Heard | |
| 8,292,888 B2 | 10/2012 | Whitman | |
| 8,298,253 B2 | 10/2012 | Charles | |
| 8,301,262 B2 | 10/2012 | Mi et al. | |
| 8,336,725 B2 | 12/2012 | Ramsey et al. | |
| 8,344,690 B2 | 1/2013 | Smith et al. | |
| 8,377,059 B2 | 2/2013 | Deville et al. | |
| 8,400,108 B2 | 3/2013 | Powell et al. | |
| 8,425,545 B2 | 4/2013 | Smith et al. | |
| 8,444,653 B2 | 5/2013 | Nycz et al. | |
| 8,449,529 B2 | 5/2013 | Bek et al. | |
| 8,487,487 B2 | 7/2013 | Dietz et al. | |
| 8,550,106 B2 | 10/2013 | Hebach et al. | |
| 8,564,242 B2 | 10/2013 | Hansford et al. | |
| 8,617,077 B2 | 12/2013 | van Groningen et al. | |
| 8,641,629 B2 | 2/2014 | Kurokawa | |
| 8,663,112 B2 | 3/2014 | Slayton et al. | |
| 2002/0165577 A1 | 11/2002 | Witt et al. | |
| 2003/0093103 A1 | 5/2003 | Malackowski et al. | |
| 2003/0109802 A1 | 6/2003 | Laeseke et al. | |
| 2003/0114851 A1 | 6/2003 | Truckai et al. | |
| 2004/0097911 A1 | 5/2004 | Murakami et al. | |
| 2004/0116952 A1 | 6/2004 | Sakurai et al. | |
| 2004/0133189 A1 | 7/2004 | Sakurai | |
| 2004/0173487 A1 | 9/2004 | Johnson et al. | |
| 2005/0021065 A1 | 1/2005 | Yamada et al. | |
| 2005/0033195 A1 | 2/2005 | Fulton, III et al. | |
| 2005/0171522 A1 | 8/2005 | Christopherson | |
| 2005/0256522 A1 | 11/2005 | Francischelli et al. | |
| 2006/0030797 A1 | 2/2006 | Zhou et al. | |
| 2006/0079829 A1 | 4/2006 | Fulton, III et al. | |
| 2006/0079874 A1 | 4/2006 | Faller et al. | |
| 2006/0079877 A1 | 4/2006 | Houser et al. | |
| 2006/0079879 A1 | 4/2006 | Faller et al. | |
| 2006/0253176 A1 | 11/2006 | Caruso et al. | |
| 2007/0027447 A1 | 2/2007 | Theroux et al. | |
| 2007/0078484 A1* | 4/2007 | Talarico et al. | 606/205 |
| 2007/0084742 A1 | 4/2007 | Miller et al. | |
| 2007/0103437 A1 | 5/2007 | Rosenberg | |
| 2007/0191713 A1 | 8/2007 | Eichmann et al. | |
| 2007/0207354 A1 | 9/2007 | Curello et al. | |
| 2007/0261978 A1 | 11/2007 | Sanderson | |
| 2007/0265613 A1 | 11/2007 | Edelstein et al. | |
| 2007/0265620 A1 | 11/2007 | Kraas et al. | |
| 2007/0282333 A1 | 12/2007 | Fortson et al. | |
| 2008/0003491 A1 | 1/2008 | Yahnker et al. | |
| 2008/0004656 A1 | 1/2008 | Livneh | |
| 2008/0057470 A1 | 3/2008 | Levy et al. | |
| 2008/0147058 A1 | 6/2008 | Horrell et al. | |
| 2008/0150754 A1 | 6/2008 | Quendt | |
| 2008/0161783 A1 | 7/2008 | Cao | |
| 2008/0173651 A1 | 7/2008 | Ping | |
| 2008/0188810 A1 | 8/2008 | Larsen et al. | |
| 2008/0200940 A1 | 8/2008 | Eichmann et al. | |
| 2008/0221491 A1 | 9/2008 | Slayton et al. | |
| 2008/0228104 A1 | 9/2008 | Uber, III et al. | |
| 2008/0255413 A1 | 10/2008 | Zemlok et al. | |
| 2008/0281301 A1 | 11/2008 | Deboer et al. | |
| 2009/0030437 A1 | 1/2009 | Houser et al. | |
| 2009/0043797 A1 | 2/2009 | Dorie et al. | |
| 2009/0076506 A1 | 3/2009 | Baker | |
| 2009/0105750 A1 | 4/2009 | Price et al. | |
| 2009/0125026 A1 | 5/2009 | Rioux et al. | |
| 2009/0137952 A1 | 5/2009 | Ramamurthy et al. | |
| 2009/0138006 A1 | 5/2009 | Bales et al. | |
| 2009/0143797 A1 | 6/2009 | Smith et al. | |
| 2009/0143798 A1 | 6/2009 | Smith et al. | |
| 2009/0143799 A1 | 6/2009 | Smith et al. | |
| 2009/0143800 A1 | 6/2009 | Deville et al. | |
| 2009/0143801 A1 | 6/2009 | Deville et al. | |
| 2009/0143802 A1 | 6/2009 | Deville et al. | |
| 2009/0143803 A1 | 6/2009 | Palmer et al. | |
| 2009/0143804 A1 | 6/2009 | Palmer et al. | |
| 2009/0143805 A1 | 6/2009 | Palmer et al. | |
| 2009/0209979 A1 | 8/2009 | Yates et al. | |
| 2009/0209990 A1 | 8/2009 | Yates et al. | |
| 2009/0240246 A1 | 9/2009 | Deville et al. | |
| 2009/0253030 A1 | 10/2009 | Kooij | |
| 2009/0264940 A1 | 10/2009 | Beale et al. | |
| 2009/0275940 A1 | 11/2009 | Malackowski et al. | |
| 2009/0281430 A1 | 11/2009 | Wilder | |
| 2009/0281464 A1 | 11/2009 | Cioanta et al. | |
| 2010/0016855 A1 | 1/2010 | Ramstein et al. | |
| 2010/0021022 A1 | 1/2010 | Pittel et al. | |
| 2010/0030218 A1 | 2/2010 | Prevost | |
| 2010/0069940 A1 | 3/2010 | Miller et al. | |
| 2010/0076455 A1 | 3/2010 | Birkenbach et al. | |
| 2010/0089970 A1 | 4/2010 | Smith et al. | |
| 2010/0106144 A1 | 4/2010 | Matsumura et al. | |
| 2010/0106146 A1 | 4/2010 | Boitor et al. | |
| 2010/0125172 A1 | 5/2010 | Jayaraj | |
| 2010/0152210 A1 | 6/2010 | Parihar et al. | |
| 2010/0160784 A1* | 6/2010 | Poland et al. | 600/453 |
| 2010/0201311 A1 | 8/2010 | Lyell Kirby et al. | |
| 2010/0211053 A1 | 8/2010 | Ross et al. | |
| 2010/0249665 A1 | 9/2010 | Roche | |
| 2010/0268221 A1 | 10/2010 | Beller et al. | |
| 2010/0274160 A1 | 10/2010 | Yachi et al. | |
| 2010/0301095 A1 | 12/2010 | Shelton, IV et al. | |
| 2011/0009694 A1 | 1/2011 | Schultz et al. | |
| 2011/0015660 A1 | 1/2011 | Wiener et al. | |
| 2011/0058982 A1 | 3/2011 | Kaneko | |
| 2011/0077514 A1 | 3/2011 | Ulric et al. | |
| 2011/0087212 A1 | 4/2011 | Aldridge et al. | |

(56) References Cited

U.S. PATENT DOCUMENTS

| | | |
|---|---|---|
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
Dietz, T. et al., Partially Implantable Vibrating Ossicular Prosthesis, Transucers '97, vol.1, International Conference on Solid State Sensors and Actuators, (Jun. 16-19, 1997) pp. 433-436 (Abstract).
"System 6 Aseptic Battery System," Stryker (2006) pp. 1-2.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
International Search Report dated Jan. 26, 2012 for Application No. PCT/US11/059220.

(56) References Cited

OTHER PUBLICATIONS

International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805
Office Action Non-Final dated Jun. 14, 2013 for U.S. Appl. No. 13/274,830.
Office Action Final dated Aug. 29, 2013 for U.S. Appl. No. 13/275,563.
Office Action Non Final dated Aug. 19, 2013 for U.S. Appl. No. 13/276,673.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 9, 2013 for U.S. Appl. No. 13/274,496.
Office Action Non-Final dated Dec. 6, 2013 for U.S. Appl. No. US 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Office Action Non-Final dated Jan. 6, 2014 for U.S. Appl. No. 13/275,514.
Office Action Final dated Sep. 27, 2013 for U.S. Appl. No. 13/276,707.
Office Action Final dated Nov. 8, 2013 for U.S. Appl. No. 13/276,745.
European Communication dated Feb. 19, 2014 for Application No. EP 11781972.2.
International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.
International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059351 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
International Preliminary Report on Patentability for Application No. PCT/US2011/059381 dated May 8, 2013.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.

(56) References Cited

OTHER PUBLICATIONS

Restriction Requirement dated Jun. 11, 2014 for U.S Appl. No. 13/151,512.
Office Action Non-Final dated Feb. 14, 2014 for U.S. Appl. No. 13/274,480.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non Final dated Jun. 19, 2014 for U.S. Appl. No. 13/274,507.
Office Action Final dated Jun. 12, 2014 for U.S. Appl. No. 13/274,516.
Office Action Final dated Feb. 28, 2014 for U.S. Appl. No. 13/275,547.
Office Action Final dated Mar. 21, 2014 for U.S. Appl. No. 13/276,673.
Office Action Non-Final dated Feb. 28, 2014 for U.S. Appl. No. 13/276,745.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, Dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2014 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
US Office Action, Notice of Allowance, dated Dec. 17, 2014 for U.S. Appl. No. 13/270,667.
US Office Action, Non-Final, dated Dec. 16, 2014 for U.S. Appl. No. 13/270,701
US Office Action, Notice of Allowance, dated Nov. 28, 2014 for U.S. Appl. No. 13/274,805.
US Office Action, Notice of Allowance, dated Dec. 19, 2014 for U.S. Appl. No. 13/276,745.
US Office Action, Non-Final, dated Dec. 8, 2014 for U.S. Appl. No. 13/277,328.

\* cited by examiner

SURGICAL INSTRUMENT SAFETY GLASSES

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pub. No. 2009/0209990 (now U.S. Pat. No. 8,657,174) entitled "Motorized Surgical Cutting and Fastening Instrument Having Handle Based Power Source," published Aug. 20, 2009, the disclosure of which is incorporated by reference herein; and U.S. Pub. No. 2010/0069940 entitled "Ultrasonic Device for Fingertip Control," published Mar. 18, 2010, the disclosure of which is incorporated by reference herein; U.S. Pat. Pub. No. 2011/0015660 (now U.S. Pat. No. 8,461,744), entitled "Rotating Transducer Mount for Ultrasonic Surgical Instruments," published Jan. 20, 2011, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; and U.S. Pat. Pub. No. 2011/0087218 (now U.S. Pat. No. 8,939,974), entitled "Surgical Instrument Comprising First and Second Drive Systems Actuatable by a Common Trigger Mechanism," published Apr. 14, 2011, the disclosure of which is incorporated by reference herein. Additionally, such surgical tools may include a cordless transducer such as that disclosed in U.S. Pat. Pub. No. 2009/0143797 (now U.S. Pat. No. 8,419,757), entitled "Cordless Hand-held Ultrasonic Cautery Cutting Device," published Jun. 4, 2009, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Medical Devices for Use With Insertable or Reclaimable Components

Figure 1:
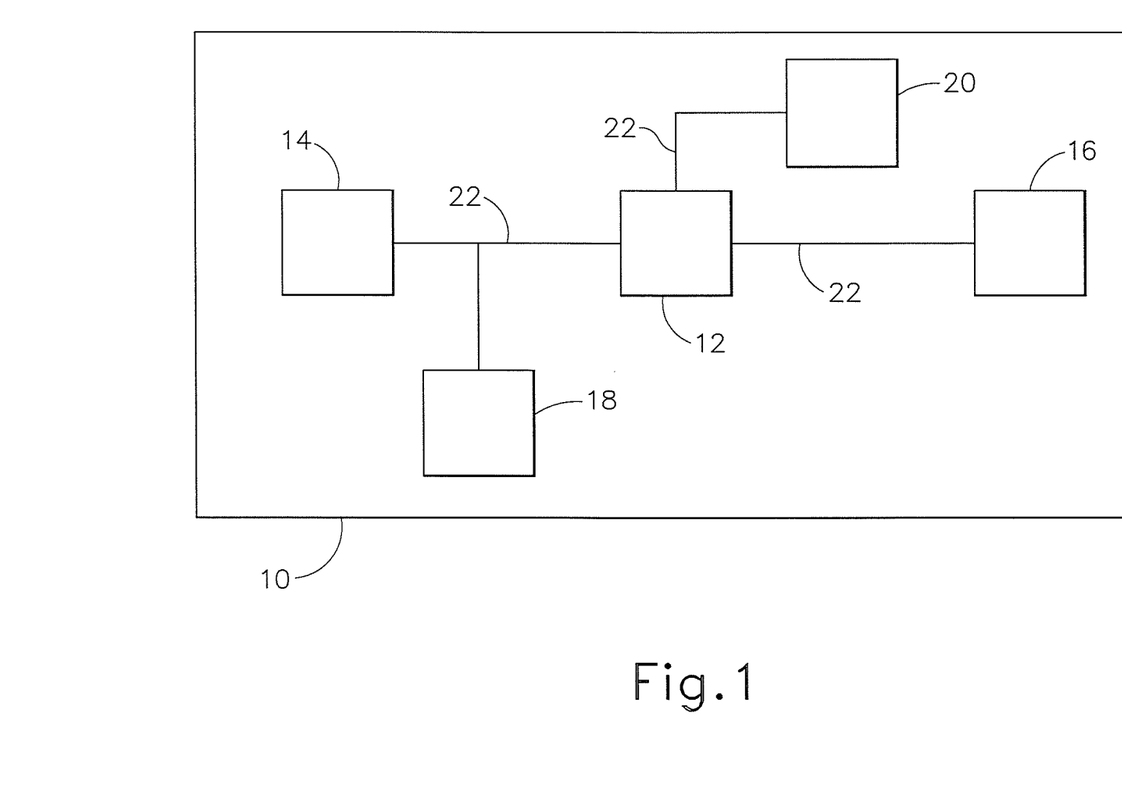
FIG. 1 depicts a schematic view of an exemplary medical device having an internal power source.

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
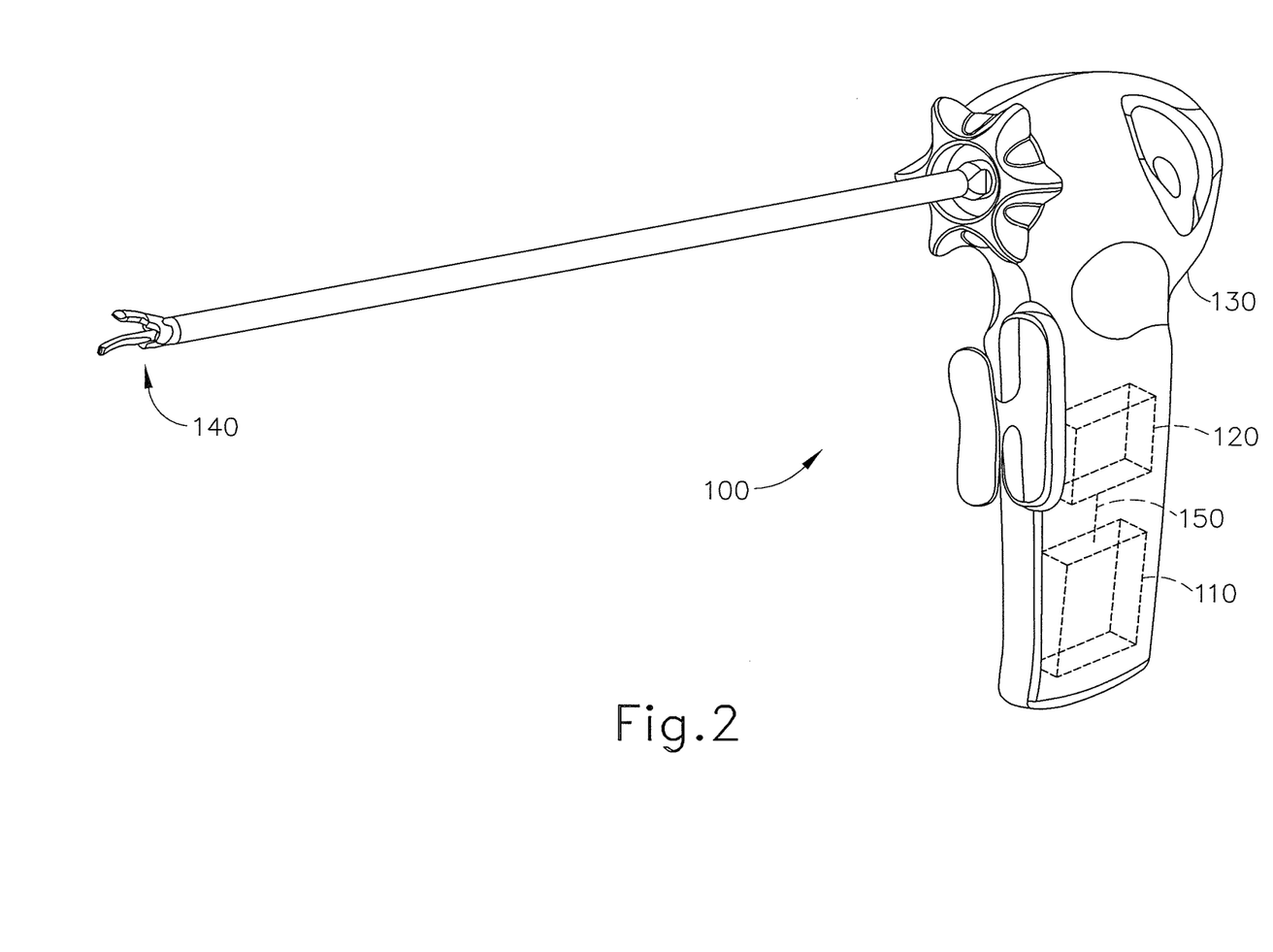
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. By way of example only, power source (110) may be constructed in accordance with the teachings of U.S. Pub. No. 2011/0087212, entitled "Surgical Generator for Ultrasonic and Electrosurgical Devices," published Apr. 14, 2011, the disclosure of which is incorporated by reference herein. In some versions, power source (110) may be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein.

While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797 (now U.S. Pat. No. 8,419,757), entitled "Cordless Hand-held Ultrasonic Cautery Cutting Device," published Jun. 4, 2009, the disclosure of which is incorporated by reference herein; U.S. Pub. No. 2010/0069940 entitled "Ultrasonic Device for Fingertip Control," published Mar. 18, 2010, the disclosure of which is incorporated by reference herein; U.S. Pub. No. 2011/0015660 (now U.S. Pat. No. 8,461,744), entitled "Rotating Transducer Mount for Ultrasonic Surgical Instruments," published Jan. 20, 2011, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

Of course, housing (130) and medical device (100) may include other configurations. For instance, housing (130) and/or medical device (100) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218 (now U.S. Pat. No. 8,939,974), entitled "Surgical Instrument Comprising First and Second Drive Systems Actuatable by a Common Trigger Mechanism," published Apr. 14, 2011, the disclosure of which is incorporated by reference herein; and U.S. patent application Ser. No. 13/151,481, entitled "Motor Driven Electrosurgical Device with Mechanical and Electrical Feedback," filed Jun. 2, 2011, the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Safety Glasses and Monitoring Systems

Examples described below relate to uses of exemplary safety glasses and monitoring systems with ultrasonic surgical instruments, though such use is possible with other instruments, such as electrosurgical devices energized with RF energy and/or any other type of instrument such as medical devices (10, 100) described above and described in the various references cited herein. Throughout this disclosure, reference numbers utilized with different alphanumeric extensions indicate similar components in different versions of a described reference (i.e., lenses (422, 422A, 422B)). Additional exemplary modifications that may be provided for medical device (10, 100) will be described in greater detail below. Various suitable ways in which the below teachings may be incorporated with medical device (10, 100) will be apparent to those of ordinary skill in the art. Similarly, various suitable ways in which the below teachings may be combined with various teachings of the references cited herein will be apparent to those of ordinary skill in the art. It should also be understood that the below teachings are not limited to medical device (10, 100) or devices taught in the references cited herein. Various other suitable devices and settings in which the below teachings may be applied will be apparent to those of ordinary skill in the art in view of the teachings herein.

A. Exemplary Monitoring Systems

Figures 3, 4:
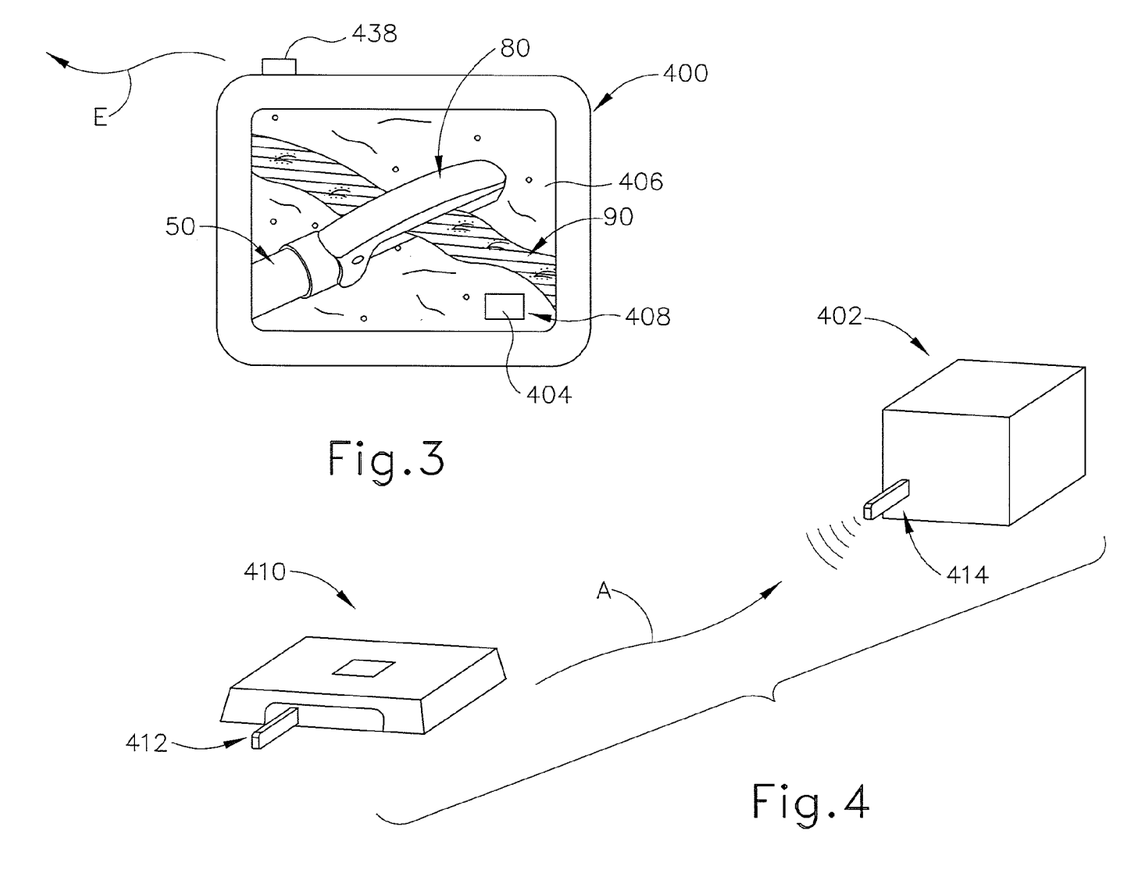
FIG. 3 depicts a elevation view of an exemplary surgical monitor displaying an end effector of the surgical instrument of FIG. 2 in use.
FIG. 4 depicts a perspective view of an exemplary generator and first wireless transmitter submitting a signal to a second wireless transmitter of a second procedure monitoring system.

FIG. 3 shows exemplary procedure or surgical monitor (400). Surgical monitor (400) may be used to broadcast video from a device such as a laparoscope, for example, during a surgical procedure. FIG. 3 shows surgical monitor (400) broadcasting video of exemplary end effector (80) of exemplary surgical instrument (50) severing tissue (90) of a patient. Surgical instrument (50) is similar in operation and construction to exemplary medical device (10, 100) described above. Surgical instrument (50) may be an ultrasonic surgical instrument or a radio frequency based surgical instrument as described above and/or in accordance with any of the references cited herein. By way of example only, an associated base station may be constructed and operable in accordance with U.S. Provisional Application Ser. No. 61/410,603, filed Nov. 5, 2010, entitled "Energy-Based Surgical Instruments," the disclosure of which is incorporated by reference herein. The base station may be, for example, procedure monitoring system (402) shown in FIG. 4, and described below. Procedure monitoring system (402) could superimpose directions or instructions (404) on surgical monitor (400) to aid a surgeon during the procedure. For example, screen (406) of surgical monitor (400) may display instructions (404) in instruction display box (408). For example, a display in box (408) may indicate that a desired seal by end effector (80) has been completed by a visual signal such as a symbol or a written message. Procedure monitoring system (402) may also be used to aid in troubleshooting issues within exemplary instrument (50) or an associated electronics module within instrument (50) before, during, or after the procedure.

As shown in FIG. 4, generator (410) provides power or other signal to instrument (50). Generator (410) includes transmitter (412) which may be connected to an external USB port of generator (410). Transmitter (412) may be, for example, a Bluetooth® wireless transmitter or fob to submit a wireless signal, depicted by arrow (A), to surgery or procedure monitoring system (402). Procedure monitoring system (402) includes receiver (414), which may be a Bluetooth® transmitter or fob that receives the signal from generator (410). Bluetooth® is a registered trademark of Bluetooth SIG, Inc. of Kirkland, Wash. Other wireless devices to transmit and receive wireless signals apparent to those of ordinary skill in the art in view of the teachings herein are within the scope of this disclosure. Procedure monitoring system (402) would not only receive a signal from generator (410), but may also include the programming and drivers needed to display information on a procedure screen such as surgical monitor (400). Procedure monitoring system (402) may be directly connected to surgical monitor (400) via a wireless or a wired connection to submit the received signal to surgical monitor (400). Additionally or alternatively, a wireless communications board or circuit board may be housed in a multi-piece handle assembly of instrument (50) to communicate information via a two-way link with a base station such as procedure monitoring system (402) of FIG. 4. In some versions, instrument (50) is battery operated and includes a transmitter. A base station communicating with instrument (50) may receive the transmitted data from instrument (50) and display the information, as described above, onto surgical monitor (400) or another troubleshooting device as will be apparent to those of ordinary skill in the art in view of the teachings herein.

Information displayable on surgical monitor (400) and received by monitor (400) as described above may include, but is not limited to including, a seal completion indicator, a generator power setting showing a minimum or a maximum power setting, for example, and/or a correct technique indicator (indicating when a technique is being improperly performed). Regarding the seal completion indicator, a generator algorithm may indicate when there is a spike in measured temperature of an ultrasonic blade, for example, of end effector (80) of instrument (50). Such a spike may indicate that the seal of tissue (90) severed by end effector (80) is complete and the blade is contacting a clamp pad or clamp arm that has pivoted toward the blade. Instructions (404) displayed in instruction display box (408) of surgical monitor (400) enable a surgeon to receive real-time feedback during the procedure regarding the status of the utilized surgical instruments, such as instrument (50), without having to look away from the surgical site presented on screen (406) of surgical monitor (400).

B. Exemplary Safety Glasses

Figure 5:
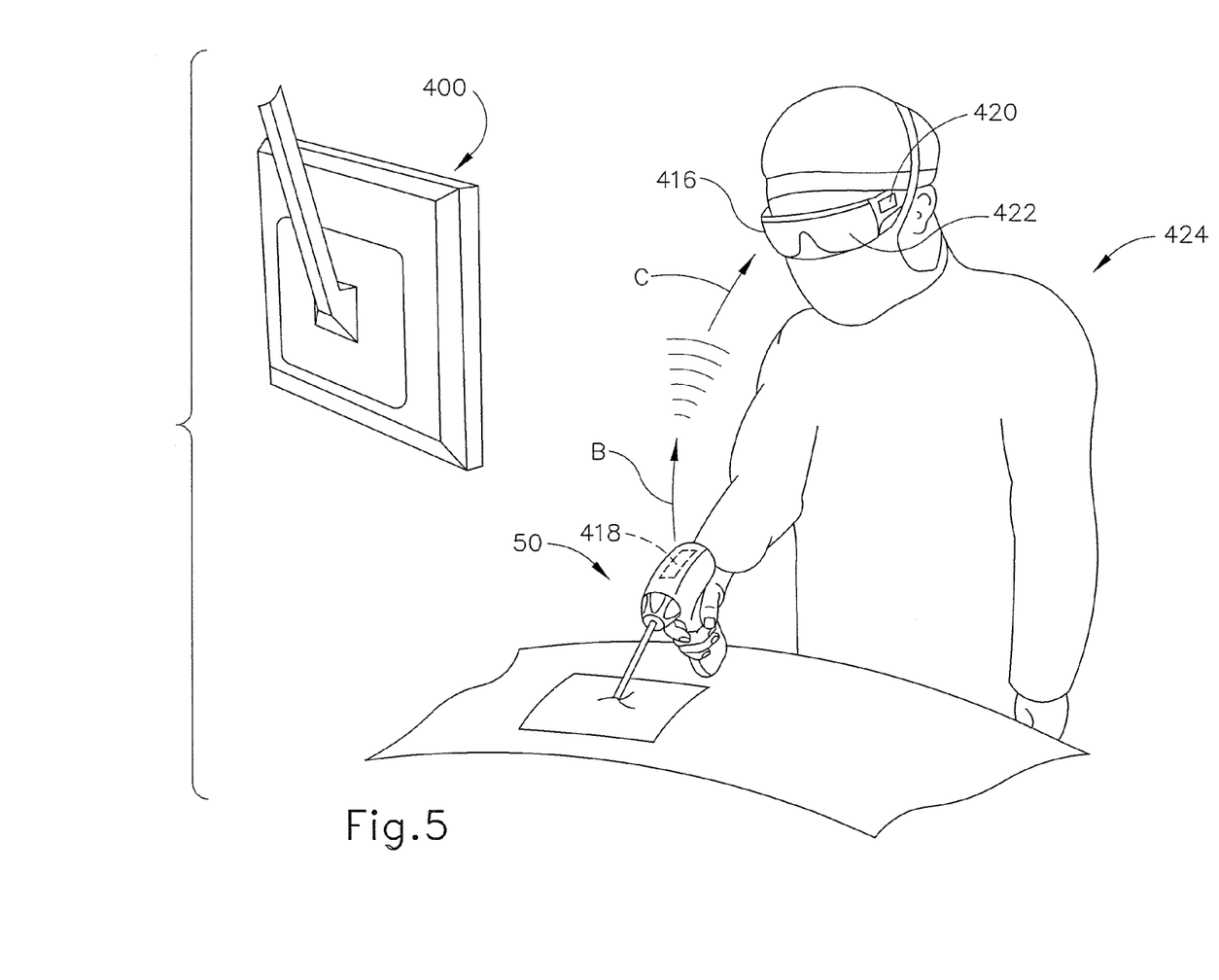
FIG. 5 depicts a perspective view of a surgeon using the exemplary surgical instrument of FIG. 2 during a surgical procedure, with the surgeon wearing a set of exemplary safety glasses.

FIG. 5 shows a version of exemplary safety glasses (416) that may be worn by a surgeon during a surgical procedure while using medical device (10, 100), for example. In use, wireless communications board (418) housed in exemplary surgical instrument (50) may communicate with wireless port (420) on safety glasses (416). Exemplary surgical instrument (50) is a battery-operated device, though instrument (50) could be powered by a cable or otherwise. Instrument (50) includes end effector (80), similar to end effector (16, 140) of medical device (10, 100) described above. Particularly, wireless communications board (418) transmits one or more wireless signals indicated by arrows (B, C) to wireless port (420) of safety glasses (416). Safety glasses (416) receive the signal, analyze the received signal, and display indicated status information received by the signal on lenses (422) to a user, such as surgeon (424), wearing safety glasses (416). Additionally or alternatively, wireless communications board (418) transmits a wireless signal to surgical monitor (400) such that surgical monitor (400) may display received indicated status information to surgeon (424), as described above.

Figure 6:
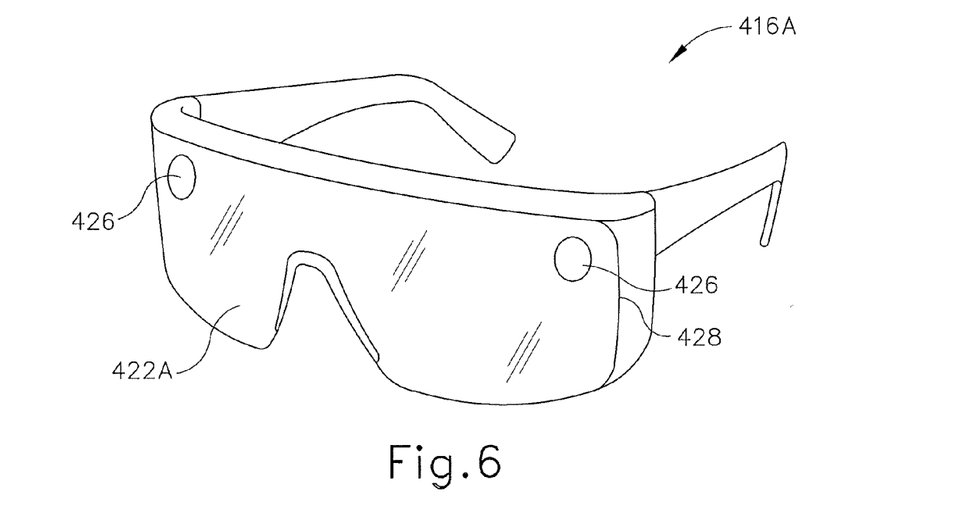
FIG. 6 depicts a perspective view of a version of the safety glasses of FIG. 5.

A version of safety glasses (416A) shown in FIG. 6 includes lighting device (426) on peripheral edges (428) of safety glasses (416A). Lighting device (426) provides peripheral-vision sensory feedback of instrument (50), with which safety glasses (416A) communicate as described below, to a user wearing safety glasses (416A). Lighting device (426) may be, for example, a light-emitted diode ("LED"), a series of LEDs, or any other suitable lighting device known to those of ordinary skill in the art and apparent in view of the teachings herein.

LEDs may be located at edges or sides of a front lens of safety glasses (416A) so not to distract from a user's center of vision while still being positioned within the user's field of view such that the user does not need to look away from the surgical site to see lighting device (426). Displayed lights may pulse and/or change color to communicate to the wearer of safety glasses (416A) various aspects of information retrieved from instrument (50), such as system status information or tissue sensing information (i.e., whether end effector (80) has sufficiently severed and sealed tissue (90)). Feedback from housed wireless communications board (418) may cause lighting device (426) to activate, blink, or change color to indicate information about the use of instrument (50) to a user. For example, a device may incorporate a feedback mechanism based on one or more sensed tissue parameters. In this case, a change in the device output(s) based on this feedback in synch with a tone change may submit a signal through wireless communications board (418) to safety glasses (416A) to trigger activation of lighting device (426). Such described means of activation of lighting device (426) should not be considered limiting as other means of indicating status information of instrument (50) to the user via safety glasses (416, 416A) are contemplated. Further, safety glasses (416A), as with other versions of safety glasses (416), may be single-use or reusable eyewear. Button-cell power supplies such as button-cell batteries may be used to power wireless receivers and LEDs of versions of safety glasses (416), which may also include a housed wireless board and tri-color LEDs. Such button-cell power supplies may provide a low-cost means of providing sensory feedback of information about instrument (50) when in use to surgeon (424) wearing safety glasses (416).

Figure 7:
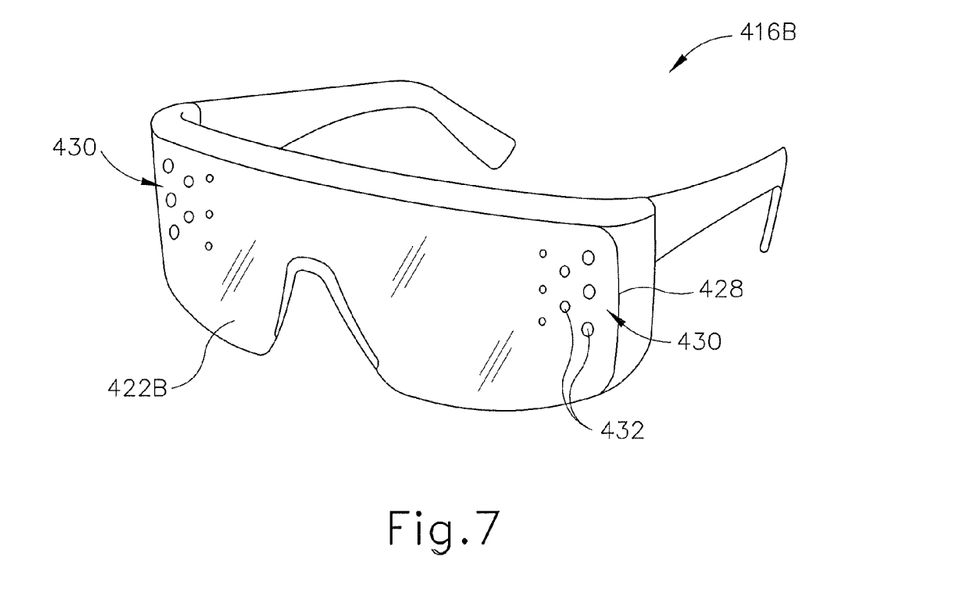
FIG. 7 depicts an elevation view of an alternative version of the safety glasses of FIG. 5.

FIG. 7 shows a version of safety glasses (416B) including lenses (422B) with edges (428) and surface modification (430). Surface modification (430) assists to "light pipe" the light from lighting device (426), as described above, to improve the ability of a user such as a surgeon to see the indicated status information. Light-piped gradual fade dots (432) positioned on edges (428) of lenses (422B) glow in a user's peripheral vision and then fade away towards the center of the user's vision when the user is wearing safety glasses (416B). LEDs may be disposed behind lenses (422) such that dots (432) may provide discrete points of light off to a side of lenses (422B), transmitting light from the LEDs. Thus, such LEDs may also or alternatively create subtle glowing light, fading light, and/or patterns of light through use of light piping, for example, and through customized surface finishing and geometry of clear lenses (422B). Use of frosted and polished sections of safety glasses (416B) may create a fade and/or soft-glow effect that may be noticeable to a wearer of safety glasses (416B) without being distracting to the wearer. Dots (432) may provide a color morph (changing color) to indicate an approaching overload of power to instrument (50). For example, color may change from a safe green, to a warning yellow, to an overload status indicator orange. Additionally or alternatively, a pulsing green light may indicate power activation of instrument (50). Further, a yellow and/or orange may indicate a cause for alarm to the user. Other information that may active dots (432) to display a change in status includes, but is not limited to, AUT condition, a tone of the device, a cycle completion status, a power activation status, a danger of overload of power status, battery life status, and the need for an alarm for other potentially dangerous status changes and received generator information. Safety glasses (416B), as well as other versions of safety glasses (416) may additionally include a piezoelectrical speaker to provide audio feedback to a wearer. Additionally, if there is no generator in the operating room, information may still be displayed for battery-operated devices used in the operating room on versions of safety glasses (416). In other words, safety glasses (416) can receive information from generator (410) and/or directly from instrument (50).

Figure 8:
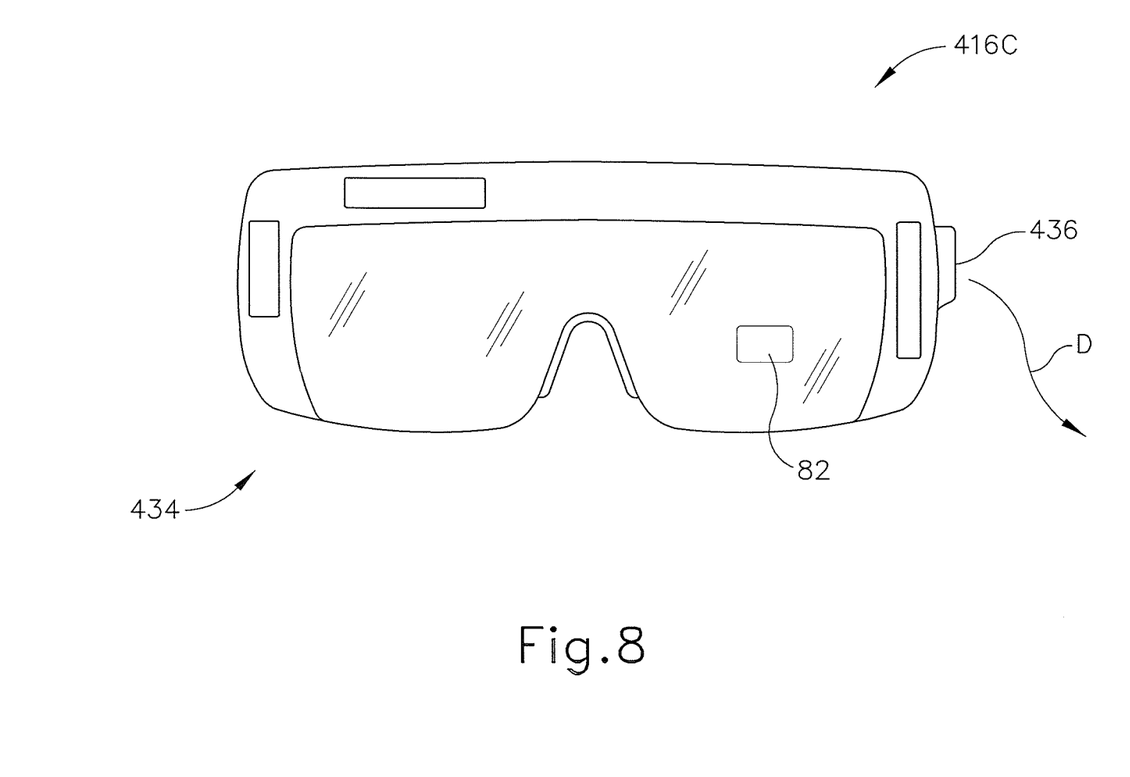
FIG. 8 depicts an elevation view of another alternative version of the safety glasses of FIG. 5.

FIG. 8 shows exemplary safety glasses (416C). Safety glasses (416C) may communicate and be used in conjunction with surgical monitor (400) to provide additional feedback to a user. Safety glasses (416C) may have a transparent color liquid crystal display ("LCD") overlay (434). LCD overlay (434) may display information to surgeon (424) as a customizable display showing pertinent information about medical device (10) such as, but not limited to, battery life, activation level status, a nerve monitoring alarm threshold indicator, and augmented tissue heat sensor information to display temperature of tissue during the procedure. For example, infrared views may appear in safety glasses (416C) as temperature of end effector (80) increases when end effector (80) is in use. The view may cause end effector (80) reflected in safety glasses (416C) as overlaid display (82), described below, to appear to turn red as temperature increases while surrounding tissue may appear to surgeon (424) wearing safety glasses (416C) to change color as well based on the temperature of the tissue.

Transponder (436) on safety glasses (416C) may be positioned on a frame arm (not shown) of safety glasses (416C), and the frame arm may house the battery and all communication systems for receipt of information from instrument (50). Transponder (436) transmits a first signal, indicated by arrow (D), which is picked up by detector (438) (FIG. 1) on surgical monitor (400). This first signal provides information on, for example, the position and orientation of safety glasses (416C). In effect, the first signal informs detector (438) on surgical monitor (400) the direction of the line of sight of surgeon (424), or rather where surgeon (424) is looking. Such information may be gathered using one or more accelerometers and/or various other types of components as will be apparent to those of ordinary skill in the art in view of the teachings herein.

Based on this orientation information and information received from an electronics module housed in medical device (10, 50, 100), for example, while submitting real-time information about instrument (50) to surgeon (424), detector (438) relays a second signal indicated by arrow (E) to transponder (436) on safety glasses (416C). The second signal causes safety glasses (416C) to display graphics on LCD overlay (434) that provide additional information to a user. For instance, based on information an electronics module housed in instrument (50) receives from end effector (80) when in use, LCD overlay (434) on safety glasses (416) may add color over an area of the vision of surgeon (424) that corresponds to end effector (80) displayed on surgical monitor (400) to indicate a temperature of end effector (80). Such an area of vision encompassing end effector (80) in use is reflected on LCD overlay (434) on safety glasses (416) to show, as FIG. 8 shows, an overlaid display (82) of end effector (80).

In use, as surgeon (424) looks through safety glasses (416C) at the ongoing procedure, surgeon (424) would see a clear view until surgeon (424) start to use instrument (50). As surgeon (424) begins to activate instrument (50), a sensor within instrument (50) transmits information such as blade temperature to safety glasses (416C). Activation of instrument (50) activates overlay (434). As surgeon (424) looks at end effector (80) on surgical monitor (400) and/or within safety glasses (416C), surgeon (424) may begin to see an infrared overlay change the color of end effector (80), or rather overlaid display (82) of end effector (80), and adjacent tissue from a normal color to an orange and then red color, for example, as the temperature of end effector (80) and/or tissue (90) increases. Such visualized information gives surgeon (424) real-time feedback as to tissue temperature and thermal spread of instrument (50) being used, for example.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical system comprising:
   (a) a surgical instrument comprising:
      (i) a body,
      (ii) a shaft extending from the body, and
      (iii) an end effector at a distal end of the shaft;
   (b) a transmitter configured to wirelessly transmit a signal associated with the end effector; and
   (c) a set of safety glasses comprising a wireless port, wherein the wireless port is configured to receive the signal from the transmitter, wherein an overlaid display of the end effector is positioned on the safety glasses when worn by a surgeon using the end effector of the surgical instrument during a surgical procedure, wherein the overlaid display is configured to change color to indicate a change in end effector temperature status based on the received signal.

2. The surgical system of claim 1, further comprising a surgical monitor, wherein the safety glasses are configured to project the signal to the surgical monitor.

3. The surgical system of claim 2, wherein the safety glasses comprise one or more LEDs, wherein the LEDs are configured to be positioned within a user's peripheral field of vision when the user is wearing the safety glasses and viewing the surgical monitor such that the LEDs do not restrict user vision of the surgical monitor and such that both the surgical monitor and the LEDs are simultaneously viewable to the user.

4. The surgical system of claim 1, wherein the safety glasses comprise a front lens and a pair of lighting devices, wherein each lighting device is disposed on a respective peripheral edge of the lens.

5. The surgical system of claim 4, wherein the lighting devices comprise one or more LEDs.

6. The surgical system of claim 5, wherein the LEDs are tri-colored.

7. The surgical system of claim 5, wherein the one or more LEDs are configured to one or both of:
   (i) display a pulsing light based on the received signal, or
   (ii) change color based on the received signal.

8. The surgical system of claim 1, wherein the safety glasses comprise at least one lighting device and a front lens including a surface modification configured to pipe light from the lighting device, wherein the surface modification is disposed on a peripheral edge of the lens.

9. The surgical system of claim 8, wherein the at least one lighting device comprises a pair of lighting devices, wherein each lighting device is disposed on a respective peripheral edge of the lens.

10. The surgical system of claim 8, wherein the at least one lighting device comprises an LED.

11. The surgical system of claim 8, wherein the surface modification comprises a series of dots configured to emit discrete points of light.

12. The surgical system of claim 8, wherein the dots are configured to emit at least one of a glow, a fade, or a pattern of light.

13. A surgical system comprising:
   (a) a surgical instrument comprising:
      (i) a body, and
      (ii) an end effector positioned distal to the body;
   (b) a transmitter configured to wirelessly transmit a signal associated with the end effector; and
   (c) a set of safety glasses comprising a wireless receiver, wherein the wireless receiver is configured to receive the signal from the transmitter, wherein the safety glasses comprise an overlaid display viewable by a surgeon using the end effector of the surgical instrument during a surgical procedure, wherein the overlaid display is configured to change color to indicate a change in end effector temperature status, based on the received signal.

14. A surgical system comprising:
   (a) a surgical instrument comprising:
      a body, and
      (ii) an end effector positioned distal to the body, wherein the end effector is operable to cut tissue, wherein the end effector comprises an ultrasonic blade or at least one RF electrode operable to apply RF energy to tissue;
   (b) a transmitter configured to wirelessly transmit a signal associated with the end effector; and
   (c) a set of safety glasses comprising a wireless receiver, wherein the wireless receiver is configured to receive the signal from the transmitter, wherein the safety glasses comprise an overlaid display viewable by a surgeon using the end effector of the surgical instrument during a surgical procedure, wherein the overlaid display is configured to change color to indicate a change in end effector temperature status, based on the received signal.

* * * * *